United States Patent [19]

Fletcher et al.

[11] 3,978,187

[45] Aug. 31, 1976

[54] METHOD OF MAKING HOLLOW ELASTOMERIC BODIES

[76] Inventors: James C. Fletcher, Administrator of the National Aeronautics and Space Administration, with respect to an invention of; Howard F. Broyles, La Crescenta; Jovan Moacanin, Los Angeles; Edward F. Cuddihy, Tujunga, all of Calif.

[22] Filed: Mar. 28, 1975

[21] Appl. No.: 563,050

[52] U.S. Cl. .............................. 264/129; 264/161; 264/219; 264/304; 264/305; 264/308; 264/310; 264/318; 264/334; 427/230; 427/385

[51] Int. Cl.² .................. B29C 13/00; B29C 25/00; B29D 23/00; B29H 3/04

[58] Field of Search .................. 264/215, 301–308, 264/310, 161, 163, 129, 219, 334, 318, 335, 259, 267; 425/DIG. 58, 93, 269, 270, 274, 275; 427/230, 384, 400, 385 B; 428/423, 474, 500

[56] References Cited

UNITED STATES PATENTS

| | | | |
|---|---|---|---|
| 1,193,883 | 8/1916 | Emery | 264/301 |
| 1,951,402 | 3/1934 | Gammeter | 264/303 |
| 2,015,632 | 9/1935 | Spanel | 264/303 |
| 2,100,571 | 11/1937 | Spanel | 264/303 |
| 2,337,116 | 12/1943 | Limbert et al. | 264/303 |
| 2,968,575 | 1/1961 | Mallonee | 264/301 |

*Primary Examiner*—Willard E. Hoag
*Attorney, Agent, or Firm*—Monte F. Mott; Wilfred Grifka; John R. Manning

[57] ABSTRACT

Annular elastomeric bodies having intricate shapes are cast by dipping a heated, rotating mandrel into a solution of the elastomer, permitting the elastomer to creep into sharp recesses, drying the coated mandrel and repeating the operation until the desired thickness has been achieved. A bladder for a heart assist pump in which a cylindrical body terminating in flat, sharp horizontal flanges fabricated by this procedure has been subjected to over 2,500 hours of simulated life conditions with no visible signs of degradation.

7 Claims, 4 Drawing Figures

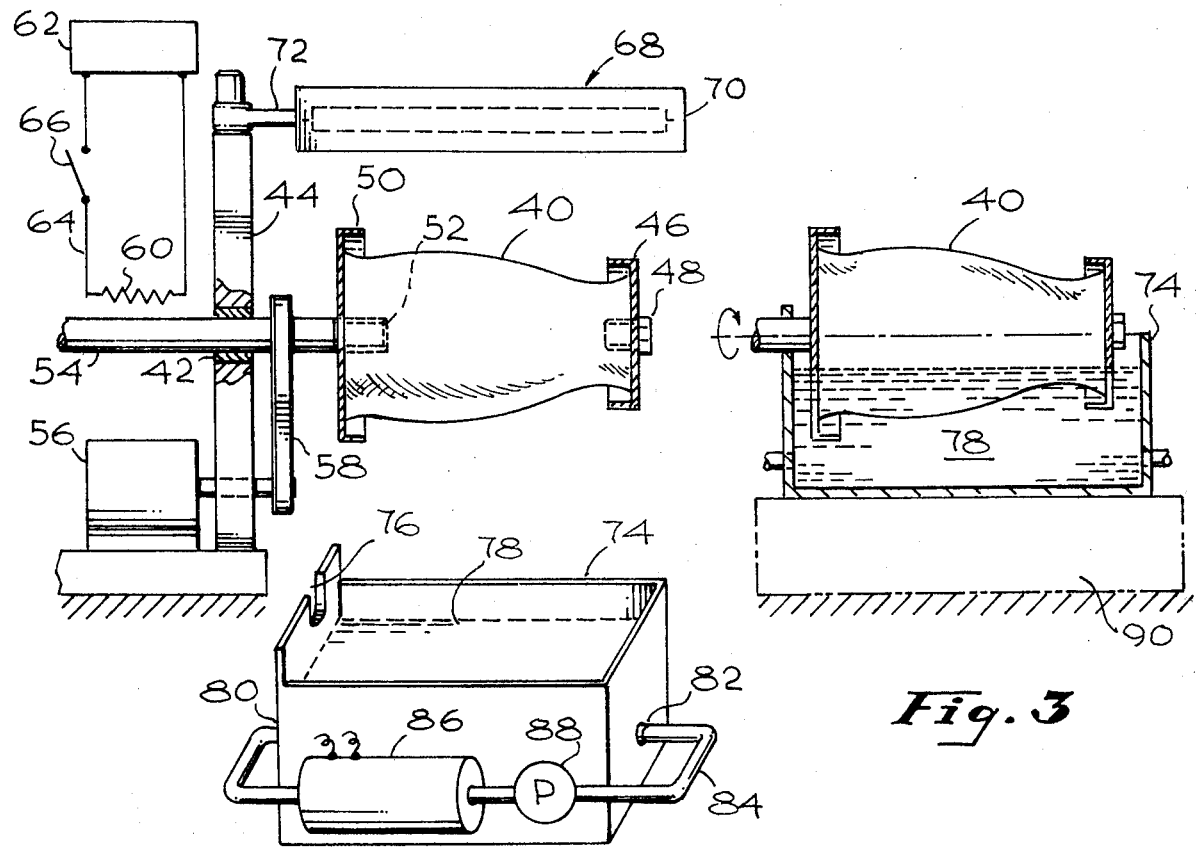
Fig. 2
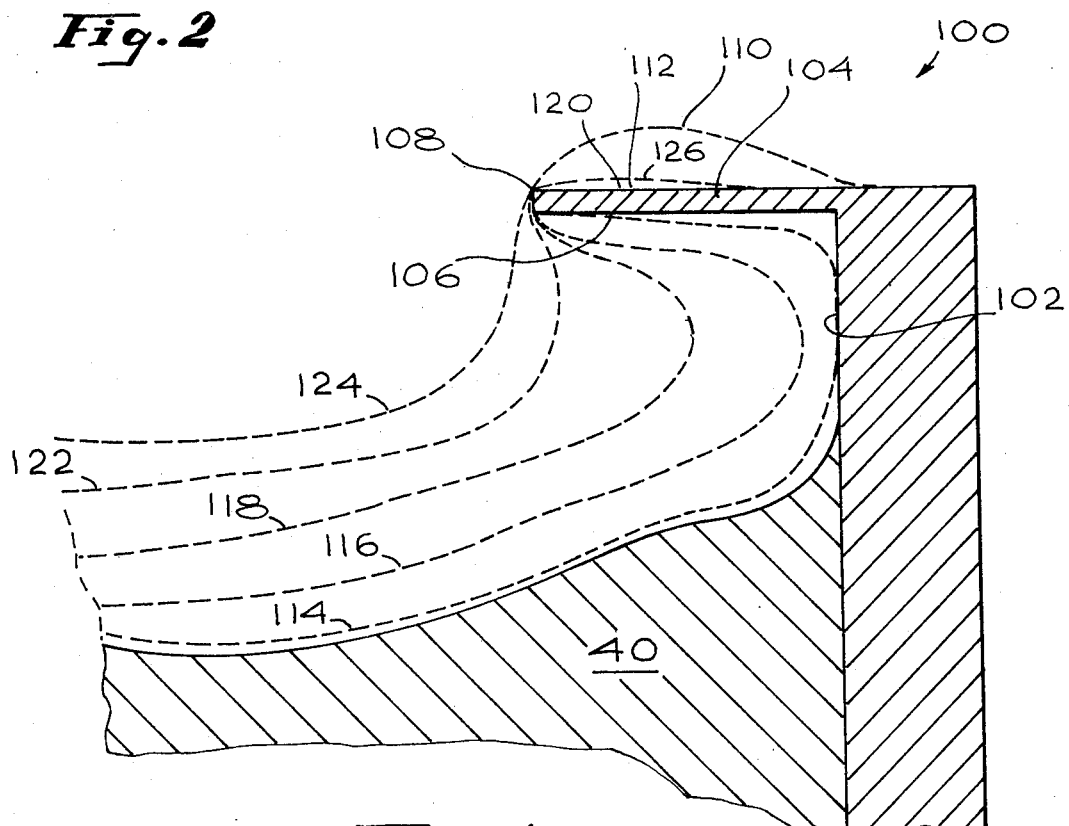
Fig. 3
Fig. 4

3,978,187

METHOD OF MAKING HOLLOW ELASTOMERIC BODIES

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to the fabrication of hollow elastomeric bodies having intricate shapes and, more particularly, to the fabrication of bladders for heart assist pumps.

2. Description of the Prior Art

A major problem in the provision of reliable prosthetics in contact with blood is the development of suitable materials for assist devices which must meet rigid requirements both mechanical and biological. They must have the requisite degree of elasticity, be rigidly non-toxic, and must be compatible with all components of blood. The materials must have an appropriate degree of elasticity for the specific end use application. They must retain this elasticity after many millions of flexing cycles in the body or other hostile biological environment and, therefore, must not be modified in that environment. They must not elicit foreign body response in the host, be rigidly non-toxic and must be compatible with blood neither causing thrombus nor clot formation destroying red cells.

Healing of the left ventricle of the heart of an animal, including man, is accelerated in certain situations if the ventricle can be relieved of some of its blood-pumping action by means of a suitable pump. One pump type requires a bladder affixed to rigid supports to serve as the active pumping element. Recently synthetic resin materials which are suitable, non-toxic substrates with full blood compatible surfaces have been developed. However, the methods for fabricating this material into a suitable bladder has not been satisfactory.

The main difficulty in fabricating these bladders is that they must be cast in a single piece since no seams, which would act as initiation sites for thrombus formation, can be tolerated. In addition, the bladder forms a virtually closed loop and can be removed from the male mold by peeling only if it is sufficiently flexible. Thermal forming by heat curing in a mold is not possible since the available materials are thermally degraded below the softening temperature. When it was attempted to spray a solution of the resin onto a mandrel, the material formed a mottled, rough product having uneven thickness and a tendency to form pinholes which is not permissible for the fabrication of an impervious bladder. The lost wax dip molding process was also unsuccessful since the bladder contains flanges with smooth, cylindrical, flat surfaces and sharp corners. This process can be utilized to separately fabricate the central body of the bladder and the flanges which are then secured by glue. This procedure introduces the possibility of later separation of the components which would result in failure and introduces a seam which serves as a site for thrombus formation and clotting.

SUMMARY OF THE INVENTION

In accordance with the invention, an annular hollow body having an integral, sharp-cornered flange attached thereto is fabricated by a multiple dip casting process in which a rotating mandrel, preferably in horizontal disposition, is repeatedly dipped into a solution of resing and dried until the desired thickness is achieved. The solution of resin is found to flow by capillary action into the casting cavity bounded by the body portion of the mandrel and the sharp edge forming boundary of the flange. Excess dried material is readily removed by stripping along the outline formed at the sharp edge of the flange.

The bladder is smooth, of uniform thickness and transparent. The bladders are pinhole free and are consistently produced with few rejects. The edges of the flanges are sharp and clean providing excellent sealing of the bladder in the pump body. The process is readily adaptable to automated mass production by provision of a line of rotating mandrels disposed over a line of resin solution tanks. Bladders fabricated by the process of this invention have been subjected to over 2,500 hours of simulated life conditions with no visible signs of degradation.

These and many other attendant advantages of the invention will become readily apparent as the invention becomes better understood by reference to the following detailed description when considered in conjunction with the accompanying drawings.

BRIEF DESCRIPTION OF THE DRAWINGS

FIG. 2 is an elevational view, partly in section, of apparatus for practicing the fabrication method;

FIG. 3 is a secional view of the rotating mandrel shown partly submerged in resin solution; and FIG. 4 is a partial sectional view of the mandrel and end cap illustrating in dotted lines the contour of the bladder after multiple dips.

DESCRIPTION OF THE PREFERRED EMBODIMENTS

Figure 1:
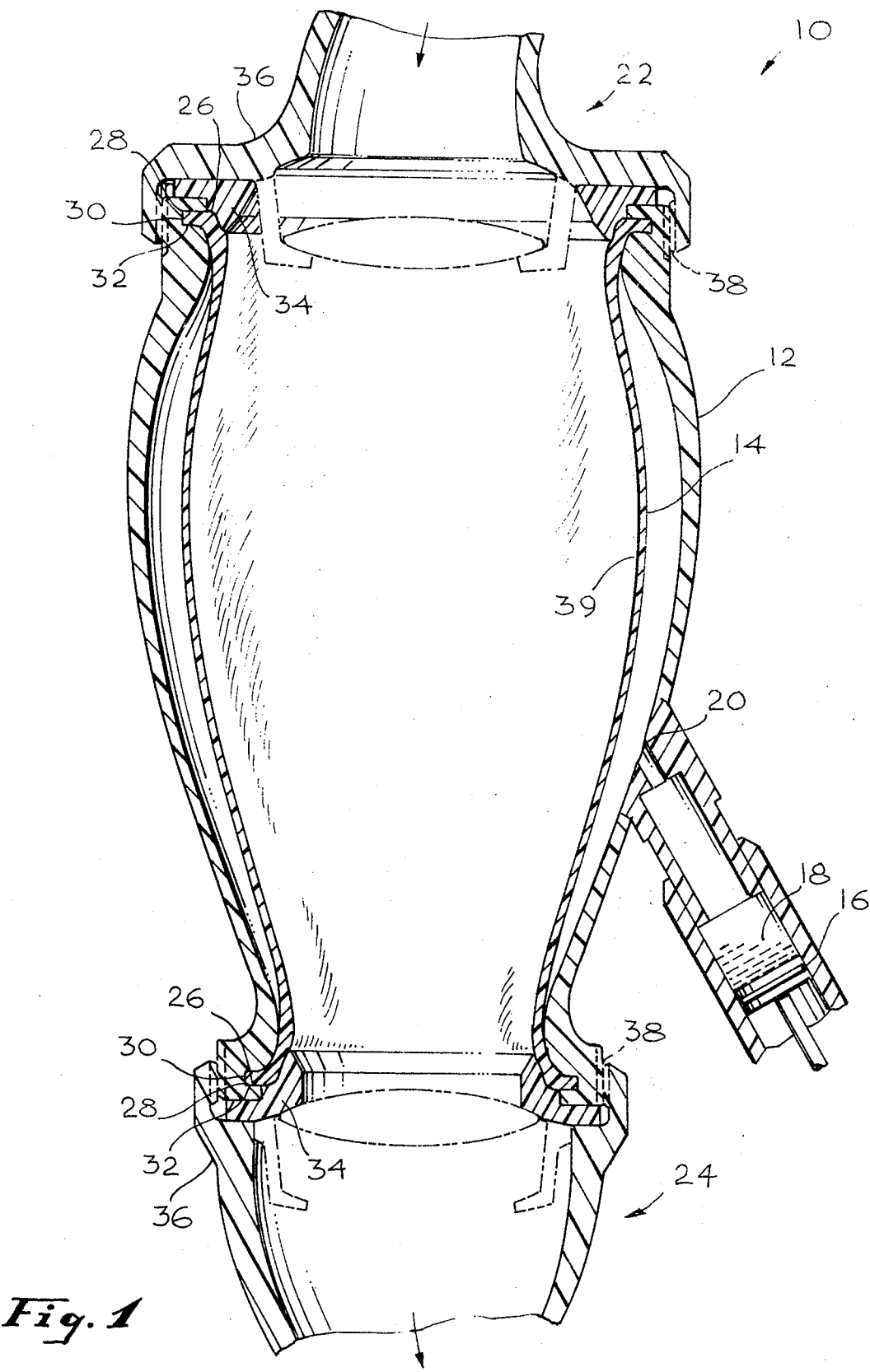
FIG. 1 is a sectional view of a cardiac assist pump including a bladder fabricated according to this invention.

Referring now to FIG. 1, the cardiac assist pump 10 includes a rigid chamber 12 in which is mounted the flexible bladder 14. The pump is designed for insertion in the aorta, the vessel being transected and the flow of blood diverted through the pump 10. Blood is pumped through the device by the action of a plunger 16 acting on hydrualic fluid 18 which enters the side orifice 20 and acts on the flexible diaphragm 14 containing the diverted blood. Blood enters through inlet 22 and exits through outlet 24. The diaphragm 14 and surrounding rigid casing 12 are each of circular cross section gradually diverging in shape from inlet to outlet.

the bladder 14 terminates at each end in a flange member 26 having a flat edge 28 and generally having a cylindrical outer surface 30. The flange 26 seats in a right-angle recess 32 formed within the interior surface of the casing member 12. The flange is sealed into the recess 32 by means of a fitting 34 which is pressed onto the flange by means of a cap member 36 which engages threads 38 on each end of the exterior surface of the casing 12. The bladder 14 must be impermeable to fluids and must have an interior surface 39 that is compatible with blood.

The bladder 14 is fabricated according to this invention in the apparatus depicted in FIG. 2. Referring now to FIG. 2, a male mandrel 40 is rotatably mounted in bushing 42 housed in a support 44. The mandrel has at least one removable cap so that the bladder can be removed without tearing after fabrication. The front cap 46 is secured to the main cylindrical mandrel by means of a threaded bolt 48. The rear cap 50 is secured to the mandrel by means of the threaded end 52 of the drive shaft 54. The drive shaft is driven by variable speed motor 56 through a belt 58.

A radiant heater 60, suitably a nichrome wire coil is disposed adjacent the shaft 54 and applies radiant energy to the metal shaft which is conducted to the mandrel 40 to heat the mandrel to a controlled, selected temperature. The heating coil 60 is connected to variable power source 62 by wires 64 containing a switch 66.

A radiant heating assembly 68 is hingedly mounted over the mandrel 40. The source 68 includes a reflector 70 in which is mounted an infrared bulb. The reflector is hingedly mounted on a support 72.

The mandrel is disposed over an open tank 74 containing a semicircular cutout 76 on the rear wall. The tank contains a body of resin solution 78 and an inlet fitting 80 and an outlet fitting 82. The solution 78 is circulated through a flexible hose circuit 84 containing a heat exchanger 86 and a pump 88 for maintaining the solution at a constant selected temperature. When the block 90, shown in dotted lines, is placed under the tank 74, the shaft 54 enters the cutout 76 and a portion of the surface of mandrel 40 is submerged in the resin solution 78.

A bladder is fabricated in the apparatus of FIG. 2 by attaching the front cap 46 to the mandrel and the rear cap to the threaded end 52 of the drive shaft. Switch 66 is closed and the mandrel 40 is heated to the selected temperature. Motor 56 is turned on to rotate the mandrel 40 and pump 88 and heat exchanger 86 are energized. When the resin solution 78 is at the desired temperature, the block 90 is placed under tank 74 for one revolution of the mandrel 40. The block is then removed and the radiant heat assembly 68 is rotated into position and energized to dry the coated, rotating mandrel, After the mandrel is dry, single revolution dipping and drying operations are continued until the desired thickness is achieved.

The mandrel is preferably mounted horizontally since this results in more uniform thickness across the length of the mandrel. It is also preferably to only submerge a portion of the mandrel, suitably at least 10% but no more than 70% of the surface, preferably less than 25% thereof, since this avoids excessive exposure to the solvent that could redissolve previous deposits. Each dip should involve an integral number of revolutions of the mandrel since a partial revolution can result in uneven thickness of deposit.

An important feature of the invention is the disposition and shape of the flange forming cavity 100 as shown in FIG. 4. The cavity is defined by the interior surface 102 of the cap and the horizontal edge member 104. The surface 102 may be flat or convex to form an integral O-ring seat. However, the interior surface 106 of the edge member 104 must be flat to form a flat edge on the flange for reliably sealing in the pump. The edge member 104 must be thin, preferably less than 10 mils, so as to form a knife edge 108 at which resin does not collect and for cleanly shearing the excess resin 110 from the flange 112.

The dotted lines in FIG. 4 represent the buildup contours of successive layers. Lines 114, 116, 118 represent 1, 5 and 8 layers respectively. As the resin is deposited, it creeps by capillary action somewhat aided by centrifugal force along surfaces 102, 106 past knife edge 108 and onto exterior surface 120. After 5–8 layers, the flange 112 is starting to fill in. After 11 layers, (contour line 122 a layer 126 of resin starts to appear on surface 120. After 14 dips (contour line 124) the flange and bladder of required thickness and a thicker layer forms on the surface 120. However, there is only a thin portion of resin at the knife edge 108. When layer 126 is peeled away, it shears from the flange along edge 109 leaving a clean, sharp edge on the flange 112.

The speed of rotation, mandrel temperature and drying temperature and time are dependent on the viscosity and solids level of the casting solution and resin. The number of layers is dependent on pick-up per dip and desired thickness.

Preferred biocompatible elastomers are solvent soluble, segmented polyether-urethanes. These polyurethanes are absent catalyst that can be leached into the blood and the physical properties can be controlled by selection of the polyether segment, chain extender and curing agent. For the heart assist pump bladder, the modulus at 20% elongation should be less than about 150 and the tensile strength should be greater than about 1,000 psi.

The segmented polyethers are synthesized from hydroxyl terminated polyalkylene oxide prepolymer having a molecular weight from 1,000 to 5,000, preferably 1,500 to 2,500, such as polytetramethylene glycol, polyethylene oxide, polypropylene oxide, polybutylene oxide or a mixture thereof. They are chain extended with diisocyanates, either aliphatic or aromatic such as methylene bis(4-phenyl-isocyanate), toluene diisocyanate and hexamethylene diisocyanate. The prepolymers are cured with diols such as butane diol or diamines such as hydrazine, hexamethylene diamine, ethylene diamine, phenylene diamine or xylylene diamine. These polymers have the following generalized structure:

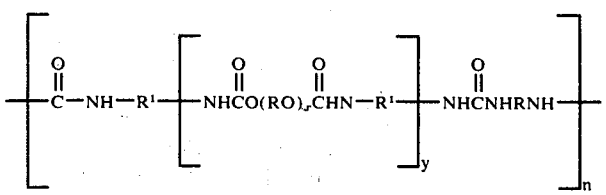

where R is alkylene from 2-4 carbon atoms, $R^1$ is the residue of the diisocyanate, $R^2$ is the residue of the diamine and $x$, $y$ and $n$ are integers.

The number of polyether molecules, $y$, per macrosegment is usually from 1-3. $x$ is the number of alkylene oxide units in each polyether molecule and n is the number of segments in the final polymer. The general reaction sequence follows:

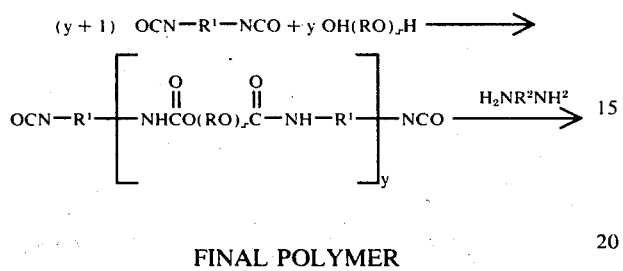

FINAL POLYMER

These materials are often referred to as segmented polyurethanes and their physical properties depend on the existence of soft polyether segments and hard urethane and urea linkages in the polymer chain. The elastomers are formed from purified reagents. Typically the polyalkylene glycol such as polypropylene glycol and diisocyanate such as MDI are prereacted in solvent such as DMSO at 100°-110°C for about three hours with stirring under nitrogen to form an isocyanate capped prepolymer. The solution is cooled to room temperature and diamine such as ethylene diamine in DMSO added. The resulting viscous solution is stirred for 30 minutes to insure complete reaction. The viscous solution is then poured into water to precipate the polymer which is then washed in several changes of water, chopped and dried in an air oven at 80°C.

An elastomer was synthesized from polypropylene glycol (PPG) of 2,000 molecular weight containing 2 PPG segment per macromolecule capped with MDI and cured with ethylene diamine. This elastomer provides satisfactory properties when fabricated into bladder forming thicknesses up to about 60 mils, typically from 20-40 mils, requiring about 10-20 single revolution dips from a solvent solution in an organic aprotic highly polar solvent such as dimethyl formamide containing 12-24% solids.

The mandrel is heated from 100°F to 140°F, preferably 120°-130°F, and the resin solution is maintained at 90°-110°F, typically about 100°F. The mandrel is rotated at 3-15 rpm, typically about 5-10 rpm, during dipping and drying. Drying temperature is also about 100°-140°F from the infrared lamp with about 2-3 hours of drying per layer. After the final layer is dried and all solvent removed, the bladder may be sterilized in a steam sterilizer without degrading the elastomer.

The blood compatability of the inner, blood-contacting surface of the bladder can be improved by grafting a thin film of hydrogel onto the surface such as poly(2-hydroxyethyl methacrylate) or polyacrylamide. For example, polyhema was coated from a solution containing in parts by volume 0.20 parts of HEMA, 0.4 parts of hydroxyethyldimethacrylate (HEDMA), 10 parts $CCl_4$ and 10 parts 2-methoxyethanol by exposure to atomic hydrogen for 1 hour. Blood compatibility during in vivo and in vitro testing of the bladders was significantly improved.

It is to be realized that only preferred embodiments of the invention have been described and that numerous substitutions, modifications and alterations are all permissible without departing from the spirit and scope of the invention as defined in the following claims.

What is claimed is:

1. A method of fabricating a smooth, hollow pinhole free elastomeric body with an integral flange attached to each end thereof, each said flange having a cylindrical peripheral surface, comprising the steps of:
   a. attaching a flange forming end cap to each end of a mandrel having an exterior male form corresponding to an internal surface of said hollow body, each cap having an interior surface portion surrounded by a peripheral flange edge member, disposing said edge members toward said mandrel, each cap having a diameter larger than said end and defining a flange forming cavity, at least one of said caps being releasably attached to the mandrel;
   b. independently heating the mandrel;
   c. disposing the mandrel horizontally and dipping 10-70% of the heated mandrel surface into a solution of elastomeric resin;
   d. recirculating the elastomer solution through a heat exchanger to control the temperature thereof;
   e. rotating the mandrel while in the solution an integral number of revolutions, to apply a layer of elastomeric resin to said male form and against inner surfaces of said edge members;
   f. removing the mandrel from the solution;
   g. drying the coated layer;
   h. repeating steps (b) to (g) until the desired thickness is achieved;
   i. removing the releasably attached end cap from one end of said mandrel and
   j. removing the hollow elastomeric body from the mandrel over said one end.

2. A method according to claim 1 further including the step of grafting a thin film of hydrogel onto the inner surface of the hollow elastomeric body.

3. A method according to claim 1 in which the mandrel has a generally cylindrical shape and includes end flange-forming cavities at each end comprising a cap member having a vertical wall joined by an outer horizontal ring and further comprising the step of flowing the resin solution across said vertical wall and onto both surfaces of said ring.

4. A method according to claim 3 in which the ring is very thin and further comprising stripping excess dried resin from the mandrel by shearing the resin along a thin edge of said ring.

5. A method according to claim 4 in which the mandrel is rotated a single revolution during each dipping to form a hollow, impervious, cylindrical bladder having integral end flanges and having a thickness of at least 20 mils.

6. A method according to claim 6 in which the solution contains 12-24% solids of a segmented polyetherurethane and the solution is heated to 90°-110°F and said mandrel is heated from 100°-140°F during dipping.

7. A method according to claim 6 in which the mandrel is rotated at from 3-15 rpm.

* * * * *